United States Patent
Knippels et al.

(10) Patent No.: US 9,555,103 B2
(45) Date of Patent: *Jan. 31, 2017

(54) BETA-LACTOGLOBULIN PEPTIDES FOR TREATING COW'S MILK PROTEIN ALLERGY

(71) Applicant: N.V. NUTRICIA, Zoetermeer (NL)

(72) Inventors: Léon Mathieu Johannes Knippels, Bunnik (NL); Johann Garssen, Nieuwegein (NL); Laura Antoinette Petronella Maria Muelenbroek, Zeist (NL)

(73) Assignee: N.V. NUTRICIA, HM Zoetermeer (NL)

( * ) Notice: Subject to any disclaimer, the term of this patent is extended or adjusted under 35 U.S.C. 154(b) by 55 days.

This patent is subject to a terminal disclaimer.

(21) Appl. No.: 14/362,545

(22) PCT Filed: Dec. 6, 2012

(86) PCT No.: PCT/EP2012/074639
§ 371 (c)(1),
(2) Date: Jun. 3, 2014

(87) PCT Pub. No.: WO2013/083691
PCT Pub. Date: Jun. 13, 2013

(65) Prior Publication Data
US 2014/0314800 A1    Oct. 23, 2014

(30) Foreign Application Priority Data

Dec. 7, 2011    (WO) ................. PCT/EP2011/006148

(51) Int. Cl.
*A61K 39/35* (2006.01)
*C07K 7/08* (2006.01)

(52) U.S. Cl.
CPC .............. *A61K 39/35* (2013.01); *A23L 33/18* (2016.08); *A23L 33/19* (2016.08); *A23L 33/40* (2016.08); *C07K 7/08* (2013.01); *A23V 2002/00* (2013.01)

(58) Field of Classification Search
CPC ...................................................... A61K 39/35
See application file for complete search history.

(56) References Cited

U.S. PATENT DOCUMENTS

| | | | |
|---|---|---|---|
| 2002/0037357 A1 | 3/2002 | Fritsche et al. | |
| 2003/0219838 A1* | 11/2003 | Johnson | 435/7.5 |
| 2004/0071714 A1* | 4/2004 | Germond et al. | 424/184.1 |
| 2009/0136615 A1 | 5/2009 | Speelmans et al. | |
| 2009/0297545 A1* | 12/2009 | Gauthier et al. | 424/185.1 |
| 2010/0303866 A1 | 12/2010 | Saint-Remy | |
| 2011/0195153 A1 | 8/2011 | Valenta et al. | |
| 2011/0262585 A1* | 10/2011 | Singhal et al. | 426/2 |
| 2012/0129935 A1 | 5/2012 | Speelmans et al. | |

FOREIGN PATENT DOCUMENTS

| | | |
|---|---|---|
| EP | 0629350 A1 | 12/1994 |
| EP | 0827697 A1 | 3/1998 |
| JP | 2010-105915 A | 5/2010 |
| WO | WO-00/42863 A1 | 7/2000 |
| WO | WO-02/24883 A2 | 3/2002 |
| WO | WO-2006/115412 A2 | 11/2006 |
| WO | WO-2008/017517 A1 | 2/2008 |
| WO | WO-2010/052939 A1 | 5/2010 |
| WO | WO-2011/069042 A2 | 6/2011 |

OTHER PUBLICATIONS

International Search Report and Written Opinion of the ISA for PCT/EP2012/074639, ISA/EP, Rijswijk, NL, mailed Feb. 14, 2013.

* cited by examiner

*Primary Examiner* — Amber D Steele
(74) *Attorney, Agent, or Firm* — Stephen T. Olson; Harness, Dickey & Pierce, P.L.C.

(57) ABSTRACT

The present invention relates to a nutritional, preferably enteral, composition for use in the treatment of cow's milk allergy in infants allergic to cow's milk containing specific beta-lactoglobulin peptides, which are able to reduce, in particular abolish the acute symptoms of cow's milk protein allergy.

20 Claims, No Drawings

SEQUENCE LISTING

<160> NUMBER OF SEQ ID NOS: 10

<210> SEQ ID NO 1
<211> LENGTH: 18
<212> TYPE: PRT
<213> ORGANISM: Bos taurus

<400> SEQUENCE: 1

Gln Lys Val Ala Gly Thr Trp Tyr Ser Leu Ala Met Ala Ala Ser Asp
1               5                   10                  15

Ile Ser

<210> SEQ ID NO 2
<211> LENGTH: 18
<212> TYPE: PRT
<213> ORGANISM: Bos taurus

<400> SEQUENCE: 2

Trp Tyr Ser Leu Ala Met Ala Ala Ser Asp Ile Ser Leu Leu Asp Ala
1               5                   10                  15

Gln Ser

<210> SEQ ID NO 3
<211> LENGTH: 18
<212> TYPE: PRT
<213> ORGANISM: Bos taurus

<400> SEQUENCE: 3

Ala Ala Ser Asp Ile Ser Leu Leu Asp Ala Gln Ser Ala Pro Leu Arg
1               5                   10                  15

Val Tyr

<210> SEQ ID NO 4
<211> LENGTH: 18
<212> TYPE: PRT
<213> ORGANISM: Bos taurus

<400> SEQUENCE: 4

Leu Leu Asp Ala Gln Ser Ala Pro Leu Arg Val Tyr Val Glu Glu Leu
1               5                   10                  15

Lys Pro

-continued

```
<210> SEQ ID NO 5
<211> LENGTH: 18
<212> TYPE: PRT
<213> ORGANISM: Bos taurus

<400> SEQUENCE: 5

Lys Val Leu Val Leu Asp Thr Asp Tyr Lys Lys Tyr Leu Leu Phe Cys
1               5                   10                  15

Met Glu

<210> SEQ ID NO 6
<211> LENGTH: 18
<212> TYPE: PRT
<213> ORGANISM: Bos taurus

<400> SEQUENCE: 6

Thr Asp Tyr Lys Lys Tyr Leu Leu Phe Cys Met Glu Asn Ser Ala Glu
1               5                   10                  15

Pro Glu

<210> SEQ ID NO 7
<211> LENGTH: 18
<212> TYPE: PRT
<213> ORGANISM: Bos taurus

<400> SEQUENCE: 7

Leu Leu Phe Cys Met Glu Asn Ser Ala Glu Pro Glu Gln Ser Leu Ala
1               5                   10                  15

Cys Gln

<210> SEQ ID NO 8
<211> LENGTH: 18
<212> TYPE: PRT
<213> ORGANISM: Bos taurus

<400> SEQUENCE: 8

Ala Leu Lys Ala Leu Pro Met His Ile Arg Leu Ser Phe Asn Pro Thr
1               5                   10                  15

Gln Leu

<210> SEQ ID NO 9
<211> LENGTH: 18
<212> TYPE: PRT
<213> ORGANISM: Bos taurus

<400> SEQUENCE: 9

Met His Ile Arg Leu Ser Phe Asn Pro Thr Gln Leu Glu Glu Gln Cys
1               5                   10                  15

His Ile

<210> SEQ ID NO 10
<211> LENGTH: 162
<212> TYPE: PRT
<213> ORGANISM: Bos taurus

<400> SEQUENCE: 10

Ala Tyr Val Thr Gln Thr Met Lys Gly Leu Asp Ile Gln Lys Val Ala
1               5                   10                  15

Gly Thr Trp Tyr Ser Leu Ala Met Ala Ala Ser Asp Ile Ser Leu Leu
                20                  25                  30

Asp Ala Gln Ser Ala Pro Leu Arg Val Tyr Val Glu Glu Leu Lys Pro
```

```
                35                    40                    45
Thr Pro Glu Gly Asp Leu Glu Ile Leu Leu Gln Lys Trp Glu Asn Asp
    50                    55                    60

Glu Cys Ala Gln Lys Lys Ile Ile Ala Glu Lys Thr Lys Ile Pro Ala
65                    70                    75                    80

Val Phe Lys Ile Asp Ala Leu Asn Glu Asn Lys Val Leu Val Leu Asp
                85                    90                    95

Thr Asp Tyr Lys Lys Tyr Leu Leu Phe Cys Met Glu Asn Ser Ala Glu
            100                   105                   110

Pro Glu Gln Ser Leu Val Cys Gln Cys Leu Val Arg Thr Pro Glu Val
            115                   120                   125

Asp Asp Glu Ala Leu Glu Lys Phe Asp Lys Ala Leu Lys Ala Leu Pro
        130                   135                   140

Met His Ile Arg Leu Ser Phe Asn Pro Thr Gln Leu Glu Glu Gln Cys
145                   150                   155                   160

His Ile
```

BETA-LACTOGLOBULIN PEPTIDES FOR TREATING COW'S MILK PROTEIN ALLERGY

CROSS-REFERENCE TO RELATED APPLICATIONS

This application is a 371 U.S. National Stage of International Application No. PCT/EP2012/074639, filed Dec. 6, 2012. This application claims priority to PCT International Application No. PCT/EP2011/006148, filed Dec. 7, 2011. The disclosures of the above applications are incorporated herein by reference.

The present invention relates to a nutritional, preferably enteral, composition for use in the treatment of cow's milk allergy in infants allergic to cow's milk, in particular whey protein, containing specific beta-lactoglobulin peptides, which are able to reduce, in particular abolish the acute symptoms of cow's milk protein allergy.

During the common process of nutrition dietary proteins are presented to the immune system via the gastro-intestinal tract without an immune response to the ingested nutrients. This unresponsiveness is called oral immune tolerance or oral tolerance. The induction of oral immune tolerance is especially relevant for infants, who after birth are exposed for the first time to dietary proteins and have to adapt to this. If in infants oral immune tolerance is not established, food allergy will occur.

About 2 to 3% of infants are allergic to cow's milk protein. For infants suffering from allergy to cow's milk protein infant formulae are on the market comprising extensively hydrolysed proteins (extensive protein hydrolysate) or even merely free amino acids as nitrogen source. In these formulae no allergenic protein or peptides are present. Thereby exposure to milk protein is avoided thus preventing an allergic reaction. This is called a secondary prevention of cows' milk allergy. However, as soon as cow's milk proteins are introduced again into the diet the infant may again suffer from allergic reaction.

Hypoallergenic formulae are on the market, comprising a partial protein hydrolysate (partially hydrolysed proteins), which have a decreased allergenicity. These formulations have the advantage that they induce orally an immunological tolerance to the intact protein, with the advantage that later on the native protein can be introduced in the diet with a reduced risk of allergic reactions. This is called primary prevention of cow's milk protein allergy and these formulae are typically used for infants at risk of developing allergy. However, for infants with diagnosed, i.e. already established cow's milk protein allergy such formulae are not suitable, since they still evoke an allergic reaction.

EP 0 629 350 discloses the use of non-allergenic whey protein hydrolysates which are said to be capable of inducing cow's milk protein tolerance.

EP 0 827 697 discloses the use of whey, that has been hydrolysed enzymatically for the preparation of compositions that induce oral tolerance to cows' milk in susceptible mammals. The whey has a level of immunological detection of allergenic proteins >=100 times less than that of unhydrolysed whey.

WO 00/42863 discloses a hypoallergenic composition for the induction of protein tolerance in infants at risk of protein allergy, comprising a non allergenic protein extensively hydrolysed basis and/or a free amino acid basis, said composition comprising as the active ingredient at least one tolerogenic peptide of the allergenic protein.

WO 02/24883 discloses the use of lactic acid bacteria to express tolerogenic peptides. The lactic acid bacteria are capable of reducing an individual's tendency to develop allergic reactions.

WO 2006/115412 discloses a liquid nutrition comprising short chains fatty acyl chains and a non-digestible, fermentable saccharide.

WO 2008/017517 discloses immunogenic peptides and their use in immune disorders.

JP 2010-105915 A discloses peptides obtained by hydrolyzing β-lactoglobulin and being for use in food and drinks.

WO 2011/069042 discloses a cow's milk peptide-containing hydrolysate and/or peptides derived thereof for tolerance induction.

However, the hypoallergenic compositions of the prior art often provide their effects only by avoiding the presence of potential allergens thereby providing only a secondary allergy prevention effect and/or they are only suitable for infants at risk of developing an allergy, but not for infants with an already established cow's milk allergy, since they would evoke an allergic reaction in such infants.

Thus, there still is a need for nutritional compositions for subjects suffering from cow's milk protein allergy with improved effects on acute symptoms. Thus, the technical problem underlying the present invention is to provide compositions, methods and means for overcoming the above-identified disadvantages, in particular that can be used to treat infants allergic to cow's milk, that means in particular that acute symptoms are reduced or even abolished when the allergenic protein is encountered again.

This technical problem is solved by the teaching of the independent claims.

Thus, the present invention provides in particular a nutritional composition for use in the treatment of cow's milk protein allergy in cow's milk protein allergic infants comprising at least one beta-lactoglobulin peptide comprising an amino acid sequence consisting of 12 to 30 amino acids and having an amino acid sequence spanning from amino acids 13 to 48 of the beta-lactoglobulin protein of SEQ ID NO 10. Preferably, the peptide has a molecular weight of below 5 kDa. Preferably, the at least one beta-lactoglobulin peptide of the present invention has a molecular weight of at most 5 kDa, in particular from 0.1 to 4.9 kDa, preferably from 0.5 to 4.9, more preferably of 2 to 4.9 kDa, most preferred of about 2.4 kDa. In a preferred embodiment the at least one beta-lactoglobulin peptide consists of 12 to 30 amino acids, preferably 14 to 25 amino acids, more preferably 16 to 20 amino acids, most preferred 18 amino acids.

The inventors surprisingly found that acute allergic reactions could be ameliorated by specific beta-lactoglobulin peptides in an animal model with allergic mice. Beta-lactoglobulin is one of two major whey proteins in the milk of cows and sheep but is not found in human milks. Often in case of cow's milk protein allergy beta-lactoglobulin is the allergen. It comprises 162 amino acid residues and a molecular weight of 18.4 kDa. In the experiments, mice had been sensitized to intact whey protein and consequently showed an acute allergic skin response after an intradermal challenge with intact whey protein, i.e. they had become whey protein allergic, which was also proven by an increase in specific IgE.

Subsequently, these mice were treated with several peptides and protein components, and it surprisingly turned out that treatment with specific peptides from a specific region of the beta-lactoglobulin protein significantly suppressed, i.e. reduced, an allergic reaction when these mice were challenged with intact whey protein again. Thus, previously allergic mice were treated with the specific beta-lactoglobulin peptides and showed a significantly reduced allergic reaction when they encountered the allergen again after treatment.

These peptides are therefore suitable for incorporation into an antiallergenic infant formula together with e.g. extensively hydrolysed protein and/or free amino acids in order to not only prevent allergic reactions by avoidance of allergens, but advantageously also to treat the allergy by reducing or ameliorating the acute allergic reaction when exposed to the allergens again. In other words these peptides are used in an oral immuno-therapy to reduce the sensitivity to the allergy.

In the context of the present invention the term "treatment" is understood to mean a therapeutic treatment of a human or animal patient, in particular infants, in terms of partially or completely curing the allergy and/or to alleviate or ameliorate symptoms of the allergy. Preferably, the treatment is an oral immuno-therapy. In the context of the present invention "treatment" is not understood to encompass the prevention or prophylaxis of an allergy, i.e. the induction of oral tolerance.

In the context of the present invention, the term "nutritional composition" relates to a composition of nutritional value which at least comprises a protein component, preferably comprises at least a protein component and a lipid component, most preferably comprises at least a protein component and a carbohydrate component and in particular at least comprises a protein component, a lipid component and a carbohydrate component. In a preferred embodiment the nutritional composition is an enteral nutritional composition. In a preferred embodiment the nutritional composition can be in liquid, semiliquid or solid form. In a preferred embodiment the solid form is in powdery form.

In the context of the present invention the term "cow's milk allergy" or "cow's milk protein allergy" is understood to mean in particular an allergy against cow's whey protein.

In the context of the present invention the term "at most 5 kDa" is understood to mean up to and including 5 kDa.

In the context of the present invention a treatment of cow's milk protein allergy is measured according to example 2 of the present teaching in the given mouse model to determine an acute allergic reaction to proteins. Accordingly, an amelioration of acute symptoms is indicated by an immediate type hyperresponsiveness (ITH) of 35 to 90%, with an acute allergic reaction having an ITH value of 100%. A significant reduction of an allergic reaction is characterised by an ITH of 0 to 30%, preferably 0 to 25%, preferably 0 to 20%, preferably 0 to 10%, most preferably 0% of the allergic reaction having an ITH value of 100%. Thus, a treatment of cow's milk protein allergy preferably means at least 15%, at least 20%, at least 30%, at least 40%, at least 50%, at least 60%, at least 70%, at least 80%, at least 90% and preferably 100% reduction of the acute allergic reaction shown by the same subject before treatment, e.g. as indicated by an ITH measured in the mouse model test as given above.

The relative value for the ITH translates into the reduction of acute allergic reactions by the following calculation formula: 100 minus ITH=reduction value. Thus, most preferably the treatment of cow's milk protein allergy according to the present invention leads to a full reduction of an acute reaction, that means a 60 to 100%, preferably 90 to 100%, preferably 95 to 100%, most preferably 100% reduction of acute allergic reactions against dietary proteins, when these proteins are encountered again.

In an analogous way the allergic reaction in humans can be quantified by the extent of the skin reactions after skin testing. This test is done by placing a drop of a solution containing a possible allergen on the skin, and a series of scratches or needle pricks allows the solution to enter the skin. If the skin develops a red, raised itchy area (called a wheal), it usually means that the person is allergic to that allergen. This is also an ITH reaction. The mean diameter of the wheal can be measured as known in the art (Maccario et al, 2003. J Allerg Clin Immunol 111, 750-756); alternatively skin thermographic measurements can be applied (Rokita et al, 2011. Med Phys 38:756-772).

In a preferred embodiment the present invention relates to a nutritional composition, preferably an enteral composition, wherein the at least one beta-lactoglobulin peptide comprises a sequence selected from the group consisting of SEQ ID NO 1, SEQ ID NO 2, SEQ ID NO 3 and SEQ ID NO 4, wherein optionally each peptide is independently substituted at its C- and/or N-terminus with 1 to 6 amino acids, preferably 1 to 5 amino acids, more preferably 1 to 4 amino acids, most preferred 1 to 3 amino acids, which can be any amino acids. In a preferred embodiment the present invention relates to a nutritional composition, wherein the at least one beta-lactoglobulin peptide consists of an amino acid sequence selected from the group consisting of SEQ ID NO. 1, SEQ ID NO. 2, SEQ ID NO. 3 and SEQ ID NO. 4.

In a particularly preferred embodiment the nutritional composition, preferably enteral composition, comprises, in particular consists of, a mixture of two, three or preferably all four of the beta-lactoglobulin peptides consisting of SEQ ID NO 1, SEQ ID NO 2, SEQ ID NO 3 and SEQ ID NO 4. That means, it is particularly preferred that the nutritional composition according to the present invention comprises all four peptides consisting of the SEQ ID NOs 1 to 4.

In accordance with the present invention the beta-lactoglobulin peptides can be chemically synthesised as known in the art, or isolated after expression by a genetically modified host such as an *E. coli* strain or *Lactobacillus* strain. Alternatively the peptides are isolated and purified from a whey protein or beta-lactoglobulin hydrolysate.

The beta-lactoglobulin peptides according to the present invention do not contain a redox motif, in particular a thioredox motif, having a reducing activity. In particular they are not substituted with such an artificial sequence.

As a further protein component, i.e. apart from the at least one beta-lactoglobulin peptide, the nutritional composition according to the present invention preferably comprises free amino acids and/or extensively hydrolyzed whey proteins. Thus, the specific beta-lactoglobulin peptides according to the present invention preferably are not part of a partial whey protein hydrolysate, but in particular are either the only protein source used or they are used together with a nitrogen source not evoking an allergic reaction, in particular free amino acids and/or an extensively hydrolysed protein, in particular an extensively hydrolysed whey protein.

Thus, according to the present invention the term "protein" or "protein component" encompasses proteins, peptides, in particular the beta-lactoglobulin peptides, free amino acids and the components of partially or extensively hydrolysed proteins. Typically, extensive protein hydrolysates have a free amino acid content of above 10 g per 100 g protein. Extensively hydrolysed protein in the present invention relates to protein which has been hydrolysed and has less than 3 wt % of peptides with a size above 5 kDa. Typically, extensively hydrolysed protein has been obtained by protease hydrolysis followed by an ultrafiltration step by filtering over a membrane with a cut off of 5 or 3 kDa.

Typically the average size of the peptides in an extensively hydrolysed protein is 2 to 3 amino acids long. Preferably these extensive protein hydrolysates comprise almost no peptides with a size over 1.5 kDa, since peptides larger than 1.5 kDa still can evoke an allergic reaction. Particularly preferred the enteral composition comprises extensively hydrolysed whey protein.

Extensively hydrolysed infant formulae are commercially available, such as Nutrilon pepti of Nutricia or Pregomin of Milupa.

Infant formulae based on free amino acids are also commercially available, for example Neocate of Nutricia.

The nutritional composition according to the present invention does not contain intact or only partially hydrolysed cow's milk protein, in particular whey protein. Instead it is preferred that the nutritional composition comprises an additional protein component selected from the group consisting of free amino acids, extensively hydrolysed whey protein and proteins from other sources such as soy, pea, rice, collagen or the like in intact or partially hydrolysed form.

Thus, the total protein content, i.e. the overall protein component, of the nutritional composition according to the present invention preferably comprises, in particular consists of, the specific beta-lactoglobulin peptides according to the present invention alone or at least one further protein component selected from the group consisting of free amino acids, extensively hydrolysed whey protein and proteins from other sources such as soy, pea, rice, collagen or the like in intact or partially hydrolysed form.

In a preferred embodiment of the present invention the present nutritional composition preferably comprises at least 10 μg, more preferably at least 30 μg, preferably at least 60 μg, preferably 10 to 5000 μg, more preferably 10 to 2000 μg and particularly preferred 20 to 1000 μg of the at least one beta-lactoglobulin peptide per g total protein.

Furthermore preferred, the nutritional composition according to the present invention comprises a total amount of protein of 5 to 25% based on dry weight of the composition. The total amount of protein refers herein to the sum of all protein components, i.e. the specific beta-lactoglobulin peptides plus all other protein components that may be present in the nutritional composition according to the present invention.

The present composition preferably contains at least 50 wt. % protein component derived from non-human milk, more preferably at least 90 wt. %, each based on dry weight of total protein.

The present nutritional, preferably enteral, composition preferably contains 5 to 25%, preferably 7 to 25%, preferably 5 to 20%, preferably 5 to 16%, preferably 5 to 12% protein based on total calories, most preferably 7.0 to 12.0% protein based on total calories of the composition. The total caloric value can be calculated based on the amount of digestible carbohydrates, fat and protein.

The present nutritional, preferably enteral, composition preferably contains 0.5 to 6.0 g, more preferably 1.0 to 3.0 g, even more preferably 1.0 to 2.5 g of protein per 100 ml of the ready to feed composition. The present nutritional, preferably enteral, composition preferably comprises at least 7.0 wt. %, more preferably at least 8.0 wt. %, most preferably at least 9 or at least 10 wt % protein based on dry weight of the total composition. Preferably, the present nutritional, preferably enteral, composition comprises at most 40 wt. %, more preferable at most 15 wt %, preferably at most 20 wt. % of protein based on dry weight of the total composition. The wt. % protein based on dry weight of the present nutritional, preferably enteral, composition is calculated according to the Kjeldahl-method by measuring total nitrogen and using a conversion factor of 6.38, preferably in case of casein, or a conversion factor of 6.25 for other proteins than casein.

Preferably, the nutritional, preferably enteral, composition according to the present invention comprises as a carbohydrate component, at least one non-digestible oligosaccharide. Advantageously and most preferred, the non-digestible oligosaccharide is water-soluble (according to the method disclosed in L. Prosky et al, J. Assoc. Anal. Chem 71: 1017-1023, 1988). Non-digestible oligosaccharides, also called prebiotics, are not digested in the intestine by the action of digestive enzymes present in the human upper digestive tract (small intestine and stomach) but instead are fermented by the human intestinal microbiota. Non-digestible oligosaccharides advantageously and unexpectedly further improve the effect of the present beta-lactoglobulin peptides in treating cow's milk protein allergy.

In a preferred embodiment the at least one non-digestible oligosaccharide is selected form the group consisting of fructo-oligosaccharide, non-digestible dextrin, galacto-oligosaccharide, xylo-oligosaccharide, arabino-oligosaccharide, arabinogalacto-oligosaccharide, gluco-oligosaccharide, glucomanno-oligosaccharide, galactomanno-oligosaccharide, mannan-oligosaccharide, chito-oligosaccharide, uronic acid oligosaccharide, sialyl-oligosaccharide and fuco-oligosaccharide.

Preferably, the nutritional composition includes a mixture of non-digestible oligosaccharides.

In a particularly preferred embodiment the non-digestible oligosaccharide contained in the nutritional composition is a fructo-oligosaccharide, preferably a short-chain, with an average degree of polymerization below 7, e.g. such as hydrolysed inulin, or a long-chain fructo-oligosaccharide, with an average degree of polymerization of above 15, more preferably above 20, e g. such as Raftilin HP, more preferably a combination of short-chain and long-chain fructo-oligosaccharide.

A fructo-oligosaccharide refers to oligosaccharides comprising β-linked fructose units, which are preferably linked by β(2,1) and/or β(2,6) glycosidic linkages, and a preferable DP between 2 and 200. Preferably, the fructo-oligosaccharide contains a terminal β(2,1) glycosidic linked glucose. Preferably, the fructo-oligosaccharide contains at least 7 β-linked fructose units. In a further preferred embodiment inulin is used as non-digestible oligosaccharide. Inulin is a type of fructo-oligosaccharide wherein at least 75% of the glycosidic linkages are β(2,1) linkages. Typically, inulin has an average chain length between 8 and 60 monosaccharide units. A suitable fructo-oligosaccharide for use in the compositions of the present invention is commercially available under the trade name Raftiline®HP (Orafti). Other suitable sources are raftilose (Orafti), fibrulose and fibruline (Cosucra) and Frutafit and frutalose (Sensus).

In a preferred embodiment the nutritional composition does not comprise galacto-oligosaccharides, in particular β-galacto-oligosaccharides. These galacto-oligosaccharides typically are derived from lactose and may contain traces of milk protein.

The present nutritional composition preferably comprises 0.05 to 20 wt. % total non-digestible oligosaccharide, more preferably 0.5 to 15 wt. %, even more preferably 1 to 10 wt. %, most preferably 2.0 to 10 wt. %, based on dry weight of the present composition.

Based on 100 ml the present nutritional composition preferably comprises 0.01 to 2.5 wt. % total non-digestible oligosaccharide, more preferably 0.05 to 1.5 wt. %, even more preferably 0.25 to 1.5 wt. %, based on 100 ml of the present composition.

In a further preferred embodiment of the present invention, the nutritional composition does not contain non-digestible oligosaccharides.

Preferably, the nutritional composition according to the present invention further comprises a lipid component and, as a carbohydrate component, at least one digestible carbohydrate.

Thus, preferably, the nutritional, preferably enteral, composition of the present invention may further comprise a lipid (also termed lipid component), in particular fat. The present nutritional, preferably enteral, composition preferably comprises as lipids vegetable lipids and/or marine oils, such as algae oils, bacterial oils, animal oils, vegetable oils or fish oils. Preferably, the composition comprises long chain polyunsaturated fatty acids, more preferably eicosapentaenoic acid (EPA) and/or docosahexaenoic acid (DHA), most preferably DHA. DHA advantageously reduces IgE synthesis and thus decreases or abolishes allergic reactions. Preferably the nutrition composition comprises at least 0.1 wt. %, more preferably 0.1 to 1 wt. % DHA based on total fatty acids. Preferably, the composition does not comprise fat or lipids from milk origin, since this fat may still comprise traces of intact milk protein.

The nutritional, preferably enteral, composition according to the present invention comprises preferably 15 to 40% of the lipid component based on dry weight of the composition.

Preferably, the at least one digestible carbohydrate may comprise one or more digestible carbohydrates which are known in the art to be suitable for use in food products, in particular infant nutritional compositions, e.g. selected from digestible polysaccharides (e.g. starch), digestible monosaccharides (e.g. glucose, fructose), and digestible disaccharides (e.g. lactose, sucrose). Particularly preferred is matodextrin. The use of maltodextrin is advantageous insofar that it has a higher molecular weight and can partially compensate for the increased osmolarity caused by free amino acids, if used.

Preferably the amount of lactose is less than 40 wt % based on total digestible carbohydrates. Preferably, the nutritional, preferably enteral, composition does not include lactose as a digestible carbohydrate.

The nutritional, preferably enteral, composition of the invention preferably comprises other components, such as vitamins and/or minerals, preferably according to international directives for infant formulae.

In a preferred embodiment of the present invention the nutritional composition consists of the at least one beta-lactoglobulin peptide as specified herein, a lipid component and a digestible carbohydrate.

In a preferred embodiment of the present invention the present nutritional composition does not comprise prebiotics.

In the context of the present invention the term "at least one beta-lactoglobulin peptide" means that two or more beta-lactoglobulin peptides are referred to thereby excluding any other component such as non-beta-lactoglobulin peptides, lipid components, carbohydrate components or combinations thereof.

In a preferred embodiment the present invention relates to a nutritional, preferably enteral, nutritional composition for use in the treatment of cow's milk protein allergy in cow's milk protein allergic infants consisting of at least one beta-lactoglobulin peptide comprising an amino acid sequence consisting of 12 to 30 amino acids and having an amino acid sequence from the region spanning from amino acids 13 to 48 of the beta-lactoglobulin protein of SEQ ID NO 10, wherein preferably the peptide has a molecular weight of at most 5 kDa, a further protein component, a lipid component, at least one digestible carbohydrate and vitamins and/or minerals.

In a preferred embodiment, the nutritional, preferably enteral, composition is an infant formula or a follow-on-formula.

In a further preferred embodiment, the nutritional, preferably enteral, composition is in the form of a dry powder or a ready to feed liquid. If the present nutritional, preferably enteral, composition is in dry form it, for instance, is a powder suitable for making a liquid composition after reconstitution with an aqueous solution, preferably with water. The present nutritional, preferably enteral, composition can also be preferably in a liquid concentrate form, which is diluted with water prior to use. If the present nutritional, preferably enteral, composition is a ready to feed liquid it already contains a liquid solvent such as water and thus does not have to be reconstituted prior to use. Preferably, if the present nutritional, preferably enteral, composition is in a liquid form, it has a viscosity below 35 mPa·s, more preferably below 6 mPa·s as measured in a Brookfield viscometer at 20° C. at a shear rate of 100 s$^{-1}$.

When the present nutritional, preferably enteral, composition is in a liquid form, the preferred volume administered on a daily basis is in the range of about 80 to 2500 ml, more preferably about 450 to 1000 ml per day.

Preferably, the nutritional, preferably enteral, composition according to the present invention comprises the following calorie distribution: the lipid component preferably provides 30 to 60% of total calories, preferably 35 to 50% of total calories, the protein component preferably provides 5 to 20%, more preferably 5 to 15% of the total calories, in particular 6 to 12% of the total calories and the digestible carbohydrate component preferably provides 25 to 65% of the total calories, preferably 40 to 60% of the total calories. The amount of total calories is determined by the sum of calories derived from protein, lipids and digestible carbohydrates.

In order to meet the caloric requirements of the infant, the present nutritional, preferably enteral, composition preferably comprises 50 to 200 kcal/100 ml liquid, more preferably 60 to 90 kcal/100 ml liquid, even more preferably 60 to 75 kcal/100 ml liquid. This caloric density ensures an optimal ratio between water and calorie consumption. The osmolarity of the present composition is preferably between 150 and 420 mOsmol/l, more preferably 260 to 380 mOsmol/l. The low osmolarity aims to reduce the gastrointestinal stress.

The present composition is not human breast milk. Preferably, the present nutritional, preferably enteral, composition is free of living or dead probiotics, in particular bifidobacteriae or lactobacillae. Since such bacteria are typically pre-cultured on milk based growth media, addition of such probiotics bears the risk of introducing traces of intact cow's milk protein. Preferably, the present nutritional, preferably enteral, composition is free of growth factors and/or cytokines. Preferably, the present nutritional, preferably enteral, composition is free of TGF, particularly TGF-beta.

The nutritional, preferably enteral, composition of the present invention is preferably for use in infants, i.e. is an infant nutritional composition. Hence, the present nutritional, preferably enteral, composition is preferably administered to a human subject during the first 3 years of life.

Preferably, the present composition is an infant formula or a follow-on-formula, or a toddler milk, that means for humans elder than infants.

In one embodiment of the use according to the present invention, the nutritional, preferably enteral, composition is for feeding or is used for feeding a human subject with an age of from 0 to 36 months. The present nutritional composition is advantageously administered to a human infant of 0 to 24 months, more preferably to a human infant of 0 to 18 months, most preferably to a human infant of 0 to 12 months.

The present nutritional, preferably enteral, composition is preferably for use in the treatment of food allergy. More preferably, the present nutritional, preferably enteral, composition is for use in the treatment of cow's milk protein allergy. Even more preferably the present nutritional, preferably enteral, composition is for use in the treatment of cow's milk whey protein allergy. The present nutritional, preferably enteral, composition is preferably for use in oral immuno-therapy.

Preferably, the present nutritional, preferably enteral, composition is for providing the daily nutritional requirements to a human, in particular for administration to, in particular for feeding, humans, in particular infants including toddlers, preferably humans suffering from cow's milk allergy, more particular infants or toddlers suffering from cow's milk allergy, in particular infants.

The present invention also relates to a nutritional composition comprising at least one beta-lactoglobulin peptide comprising an amino acid sequence consisting of 12 to 30 amino acids and having an amino acid sequence from the region spanning from amino acids 13 to 48 of the beta-lactoglobulin protein of SEQ ID NO. 10, wherein the at least one beta-lactoglobulin peptide is for use in the treatment of cow's milk protein allergy and cow's milk protein allergic infants and wherein the further components of said nutritional composition are as specified above.

The present invention also relates a nutritional composition comprising a protein component, a lipid component and digestible carbohydrates, wherein the protein component comprises, in particular consists of, i) the at least one beta-lactoglobulin peptide according to any one of claims 1 to 4 and ii) at least one selected from the group consisting of extensively hydrolysed protein and free amino acids, wherein in sum of i) and ii) accounts for at least 95 wt. %, preferably at least 96 wt. %, preferably at least 97 wt. %, more preferably at least 98 wt. %, most preferably at least 99 wt. % of the protein component, and wherein the lipid component comprises at least 0.1 wt. % DHA based on total fatty acids.

In one embodiment the present invention relates to a nutritional composition comprising a protein component, a lipid component and digestible carbohydrates, wherein the protein component comprises, in particular consists of, at least 95 wt. %, preferably at least 96 wt. %, preferably at least 97 wt. %, more preferably at least 98 wt. %, most preferably at least 99 wt. % of the at least one beta-lactoglobulin peptide according to the present invention and at least one selected from the group consisting of extensively hydrolysed protein and free amino acids, and wherein the lipid component comprises at least 0.1 wt. % DHA based on total fatty acids.

In a preferred embodiment the nutritional composition comprises at least one non-digestible oligosaccharide, wherein the non-digestible oligosaccharide is preferably a short-chain or long-chain fructo-oligosaccharide.

In a preferred embodiment the nutritional composition comprises 10 to 5000 µg of the at least one beta-lactoglobulin peptide per g total protein. In a preferred embodiment the present nutritional composition preferably comprises at least 10 µg, more preferably at least 30 µg, preferably at least 60 µg, preferably 10 to 5000 µg, more preferably 10 to 2000 µg and particularly preferred 20 to 1000 µg of the at least one beta-lactoglobulin peptide per g total protein.

Preferably, the nutritional composition according to the present invention comprises a total amount of protein of 5 to 25% based on dry weight of the composition.

The present nutritional composition preferably is an infant formula or a follow-on-formula. Particularly preferred, the nutritional composition is an infant formula or a follow-on-formula for use in feeding cow's milk protein allergic infants.

All compositions and substances identified herein to be suitable and designed for a use according to the present invention are to be understood also to be suitable and designed for being applied in methods of treatment or methods for feeding a subject, in particular a human subject, in need thereof.

In the context of the present invention all relative amounts given in percentage (%) of an indicated overall composition add up to 100% of the indicated overall composition.

In the context of the present invention the wordings "to comprise" and "to contain" and their conjugations are used in one preferred embodiment in their non-limiting sense to mean that items following the wording are included, but items not specifically mentioned are not excluded. In the context of the present invention the wording "to comprise" or "to contain" and their conjugations are used in another preferred embodiment in its limiting sense to mean that items following the wordings are included and items not specifically mentioned are excluded thereby equalling the meaning of the wording "to consist" and its conjugations.

Reference to an element of the present invention, particularly composition or method, by the indefinite article "a" or "an" does not exclude the possibility that more than one of the element is present, unless the context clearly requires that there be one and only one of the elements. The indefinite article "a" or "an" thus usually means "at least one".

Further preferred embodiments are the subject matter of the subclaims.

The invention will be further described by way of the non-limiting examples.

SEQ ID NO 10 shows the amino acid sequence of the complete bovine beta-lactoglobulin protein with 162 amino acids in total. The region within the beta-lactoglobulin protein spanning from amino acids 13 to 48 has the sequence: Gln Lys Val Ala Gly Thr Trp Tyr Ser Leu Ala Met Ala Ala Ser Asp Ile Ser Leu Leu Asp Ala Gln Ser Ala Pro Leu Arg Val Tyr Val Glu Glu Leu Lys Pro.

EXAMPLE 1

Selection of Peptides 18 amino-acid-long synthetic peptides with 12 amino-acid overlap spanning the B variant of beta-lactoglobulin and six synthetic peptides of the A variant of beta-lactoglobulin were obtained from JPT Peptide Technologies (Berlin, Germany).

Peptides were synthesized and pre-screened with an assay with T cell lines. Twenty-five 18-Epstein Barr Virus (EBV)-transformed B cells were cultured in RPMI 1640-GlutaMAX™-I supplemented with 10% heat-inactivated FBS and 2% Pen/Strep. Cow's milk-specific T cell lines (TCL) were generated as described previously by Schade et al. (2000, J Allerg. Clin. Immunol. 106: 1155-62). The TCLs were cultured in Yssel's medium containing 2% HS, 2% Pen/Strep, 1% Glut, 50 IU/ml IL-2 and 50 IU/ml IL-4 and were re-stimulated every two weeks with cow's milk to maintain them in culture. For the re-stimulation, autologous EBV-transformed B cells were pre-incubated overnight with 50 µm/ml cow's milk protein mixture. Subsequently, the B cells were irradiated and added to the TCLs.

Peptide-specific T cell proliferation was tested as described before by Ruiter et al. (2006, Clin Exp Allergy 36:303-10). In short, irradiated EBV-transformed B cells ($4\times10^4$/well) were pre-incubated overnight in triplicate in 96-well U-plates with 50 µg/ml major allergen or 10 µg/ml synthetic peptide (either a mixture of 2 or 3 peptides, or single peptides). Whey protein (prolacta) was obtained from Lactalis (Laval, France). Caseinate was purchased from FrieslandCampina Domo (Amersfoort, The Netherlands). For the cow's milk protein mixture, prolacta and caseinate were mixed in a 1:1 ratio. Also alpha-lactalbumin (alpha-LAC) and beta-lactoglobulin (beta-LG) were tested as controls. Subsequently, $4\times10^4$ T cells were added to the wells and cultured for 24 hours. The next day, tritiated thymidine (1 µCi/well) was added. After 18 hours, the cells were harvested on glass fibre filters and the [$^3$H]-TdR incorporation was measured using a Microbeta2 plate counter (Perkin Elmer, Waltham, Mass., USA). The incorporation was expressed as counts per minute (cpm) and background proliferation of EBV B cells was subtracted. All tests were performed in Yssel's medium with 2% Pen/Strep and 1% Glut and incubations were done at 3° C. in a humidified 5% $CO_2$ atmosphere. Each TCL was tested at least three times.

The peptides having the highest T cell reactivity were selected for further testing in an animal model. These nine peptides were derived from beta-lactoglobulin. Peptide mix 1-4 had the best effect.

TABLE 1

Sequence information of the peptides

| Peptide | Sequence | Amino acids (AA) beta-lactoglobulin |
|---|---|---|
| 1 | Gln Lys Val Ala Gly Thr Trp Tyr Ser Leu Ala Met Ala Ala Ser Asp Ile Ser (SEQ ID NO 1) | AA 13-30 |
| 2 | Trp Tyr Ser Leu Ala Met Ala Ala Ser Asp Ile Ser Leu Leu Asp Ala Gln Ser (SEQ ID NO 2) | AA 19-36 |
| 3 | Ala Ala Ser Asp Ile Ser Leu Leu Asp Ala Gln Ser Ala Pro Leu Arg Val Tyr (SEQ ID NO 3) | AA 25-42 |
| 4 | Leu Leu Asp Ala Gln Ser Ala Pro Leu Arg Val Tyr Val Glu Glu Leu Lys Pro (SEQ ID NO 4) | AA 31-48 |
| 5 | Lys Val Leu Val Leu Asp Thr Asp Tyr Lys Lys Tyr Leu Leu Phe Cys Met Glu (SEQ ID NO 5) | AA 91-108 |
| 6 | Thr Asp Tyr Lys Lys Tyr Leu Leu Phe Cys Met Glu Asn Ser Ala Glu Pro Glu (SEQ ID NO 6) | AA 97-114 |
| 7 | Leu Leu Phe Cys Met Glu Asn Ser Ala Glu Pro Glu Gln Ser Leu Ala Cys Gln (SEQ ID NO 7) | AA 103-120 |
| 8 | Ala Leu Lys Ala Leu Pro Met His Ile Arg Leu Ser Phe Asn Pro Thr Gln Leu (SEQ ID NO 8) | AA 139-156 |
| 9 | Met His Ile Arg Leu Ser Phe Asn Pro Thr Gln Leu Glu Glu Gln Cys His Ile (SEQ ID NO 9) | AA 145-162 |

Animal Testing

Shortly prior to the experiment, the peptides were suspended in PBS. The peptides were combined in three mixtures, namely peptides 1-4 in mixture 1, peptides 5-7 in mixture 2 and peptides 8 and 9 in mixture 3 (see table 1, above). The final concentration of each peptide in the mixture was 8 mg/ml.

Three-week-old pathogen free female C3H/HeOuJ mice (Charles River Laboratories, Maastricht, the Netherlands) were used for this experiment. The mice were maintained on cow's milk protein free standard mouse chow (AIN-93G soy, Special Diets Services, Wijk bij Duurstede, the Netherlands). They were housed in the animal facility at the Utrecht University and treated according to the guidelines of the Dutch Committee of Animal Experiments.

The mice (n=6 per group) were treated orally using a blunt needle with 0.5 ml of the peptide mixtures or PBS in the week prior to the sensitization (from day −7 until day −2). During this week (day −7 until day 0) the mice received the standard AIN-93G (control) diet. On days 0, 7, 14, 21 and 28, the mice were orally sensitized with 20 mg whey and 10 µg CT in 0.5 ml PBS. The non-sensitized mice were treated with 10 μg CT in 0.5 ml PBS. Five days after the last sensitization, the mice received an intradermal challenge in the ear pinnae with 10 μg whey in 20 μl PBS. Before and 1 h after the challenge, the ear thickness was measured using a digital micrometer (Mitutoyo, Veenendaal, the Netherlands). The difference in the ear thickness (ear swelling) is an indication for the acute allergic response and is expressed as delta μm. It turned out that in this pretreatment protocol peptide mixture 1 was effective.

EXAMPLE 2

Treatment with Beta-Lactoglobulin Peptides in Whey Protein Allergic Mice Results in Absence of an Allergic Reaction Three-week-old pathogen free female C3H/HeOuJ mice (Charles River Laboratories, Maastricht, The Netherlands) were used for this experiment. The mice were maintained on cow's milk protein free standard mouse chow (AIN-93G soy, Special Diets Services, Wijk bij Duurstede, the Netherlands). They were housed in the animal facility at the Utrecht University and treated according to the guidelines of the Dutch Committee of Animal Experiments.

Whey was obtained from DMV International (Veghel, the Netherlands). A partial whey hydrolysate (pWH) was manufactured at Danone Research Centre for Specialised Nutrition by enzymatic hydrolysis under the following specified conditions. 19.5 kg of demineralised water (in the following "demi water") of 12° C. was put into a bin and mixed with 4.1 kg demineralised whey (Deminal, Friesland Foods Domo) and 1.41 kg of lactalis Nutriwhey800 (DMV Campina) for 30 minutes. The solution was given a heat treatment of 2 minutes at 78° C. The product was cooled to 60° C. after the heat treatment. 15.6 g $Ca(OH)_2$, 1.84 g $Mg(OH)_2$, 16.1 g KOH and 15.25 g NaOH was dissolved in 235 ml demi water to obtain a base solution. The hydrolysis tank was filled with 12 kg of the heat treated whey solution and stirred. The temperature was kept at 58° C. The base solution was used to adjust the pH of the hydrolysis tank to pH of 7.75. 16.8 g Alcalase and 3.8 g Flavourzyme was mixed and added to the fermentor quickly. The base solution was used to regulate the pH at 7.75. The hydrolysis took place for 180 minutes. The enzymatic process was stopped by fast cooling and the solution was frozen. The pWH was further characterized by analysis of the peptide by means of size exclusion high pressure liquid chromatography. The size distribution was as follows: 85 wt. %<1 kD, 8 wt. % 1 to <2 kDa, 4 wt. % 2 to <5 kDa, 1 wt. % 5 to <10 kDa, 0.6 wt. % 10 to 20 kDa and 1.4 wt. %>20 kDa.

Cholera toxin (CT) was obtained from Quadratech Diagnostics (Epsom, United Kingdom). Phosphate-buffered saline (PBS) was obtained from Cambrex Bio Science (Verviers, Belgium).

Mice (n=6 per group) were orally sensitized with 20 mg whey and 10 μg CT in 0.5 ml PBS on days 0, 7, 14, 21 and 28. The non-sensitized mice were treated with 10 μg CT in 0.5 ml PBS. Five days after the last sensitization, blood was withdrawn from the mice and plasma was collected. Whey protein-specific IgE levels were measured to determine whether the sensitization was successful. Indeed the mice had become allergic to whey protein, since an increase in whey protein specific IgE was observed.

One week later, the treatment was started. Mice were treated orally 14× during four weeks (first week 5× per week, then 3× per week) with a) 0.5 ml 100 mg/ml whey, b) 0.5 ml 1 mg/ml whey, c) 0.5 ml 100 mg/ml pWH, d) 0.5 ml 1 mg/ml pWH or e) 0.5 ml of a mixture of the synthetic peptides 1, 2, 3 and 4. Concentration of each peptide in this mixture was 80 μg/ml.

Three days after the last treatment the mice received an intradermal challenge in the ear pinnae with 10 μg whey in 20 μl PBS. Before and 1 h after the challenge, the ear thickness was measured using a digital micrometer (Mitutoyo, Veenendaal, the Netherlands). The difference in the ear thickness (ear swelling) is an indication for the acute allergic response measured as immediate type hyperresponsiveness (ITH) and is expressed as delta μm. Again whey protein specific IgE was determined. Also whey protein-specific IgG1 and IgG2a was determined.

Results are shown in table 2. Treatment with whey protein (in 100 mg/ml or 1 mg/ml) or with PBS showed a significant increase of the allergic response in whey protein allergic mice challenged with whey protein, compared with non allergic mice. Treatment with pWH (in 100 mg/ml or 1 mg/ml) resulted in an allergic response in allergic mice which was not statistically different from the control non allergic mice, nor from the control allergic mice. The IgE measurements were in line with those observed for oral immuno-therapy.

Treatment with the peptide mixture of the present invention in allergic mice, however, resulted in a significant reduction of allergic reaction compared to non-treated allergic mice or the whey protein treated allergic mice.

The peptide mixture of the present invention therefore is able to treat symptoms of an acute allergic reaction in allergic mice.

TABLE 2

Ear swelling response 1 h after intradermal challenge

| Group | Mean ΔITH μm (S.E.) | Relative ITH |
|---|---|---|
| CT + PBS | 22.29 (4.50) | 0% |
| CT/whey + PBS | 122.7 (14.2)* | 100% |
| CT/whey + 100 mg/ml whey | 110.9 (12.8)* | 88.2% |
| CT/whey + 1 mg/ml whey | 88.79 (10.16)* | 66.2% |
| CT/whey + 100 mg/ml pWH | 66.69 (12.67) | 44.2% |
| CT/whey + 1 mg/ml pWH | 52.56 (3.95) | 30.1% |
| CT/whey + Peptide mix | 41.25 (6.87)# | 18.9% |

*$p < 0.05$ compared to negative control (CT + PBS)
$p < 0.05$ compared to positive control (CT/whey + PBS) and whey treated group (CT/whey + 100 mg/ml whey).

EXAMPLE 3

Infant Formula for Cow's Milk Allergic Infants

Energy density: 0.6-0.77 kcal/ml; Lipids: 5.5 to 7 g/100 ml ready to use formula. Protein is present in the form of free amino acids and the beta-lactoglobulin peptides of the present invention. Per g protein about 100 μg peptide mix as tested in example 2 is present.

| Nutrition Info. | Per 100 g Powder | Per 100 kcal * | Per 100 ml** |
|---|---|---|---|
| Energy kJ | 2918 | 413 | 292 |
| kcal | 707 | 100 | 70.7 |

| | | | |
|---|---|---|---|
| Protein g | 15.2 | 2.1 | 1.5 |
| Carbohydrate g | 7.6 | 1.1 | 0.76 |

| Typical Amino Acid Profile | g/100 g Powder |
|---|---|
| L-Alanine | 0.5 |
| L-Arginine | 0.53 |
| L-Aspartic Acid | 1.1 |
| L-Cystine | 0.42 |
| L-Glutamic Acid | 3.3 |
| Glycine | 0.29 |
| L-Histidine | 0.46 |
| L-Isoleucine | 0.75 |
| L-Leucine | 1.5 |
| L-Lysine | 1.2 |
| L-Methionine | 0.43 |
| L-Phenylalanine | 0.76 |
| L-Proline | 1.6 |
| L-Serine | 0.81 |
| L-Threonine | 0.73 |
| L-Tryptophan | 0.41 |
| L-Tyrosine | 0.81 |
| L-Valine | 0.99 |
| L-Carnitine | 0.03 |
| Taurine | 0.05 |

| Carbohydrate Profile Carbohydrate Powder | g/100 g | g/100 g |
|---|---|---|
| Dextrose | 1.9 | 0.14 |
| Lactose | 0.4 | 0.03 |
| Maltose | 6.7 | 0.51 |
| Maltotriose | 9.5 | 0.72 |
| Higher Saccharides | 81.5 | 6.2 |

The composition further comprises vegetable and microbial fat, with 0.2 wt % DHA based on total fat.

---

The invention claimed is:

1. A nutritional composition for use in the treatment of cow's milk protein allergy in cow's milk protein allergic infants, the nutritional composition comprising at least one beta-lactoglobulin peptide comprising an amino acid sequence consisting of 18 to 30 amino acids and having an amino acid sequence selected from the group consisting of SEQ ID NO 1, SEQ ID NO 2, and SEQ ID NO 3, wherein the composition comprises 10 to 5000 µg of the at least one beta-lactoglobin peptide per g of total protein in the composition.

2. The nutritional composition for use in the treatment of cow's milk protein allergy in cow's milk protein allergic infants according to claim 1, comprising as a further protein component free amino acids and/or extensively hydrolyzed proteins.

3. The nutritional composition for use in the treatment of cow's milk protein allergy in cow's milk protein allergic infants according to claim 1, comprising at least one non-digestible oligosaccharide selected form the group consisting of fructo-oligosaccharide, non-digestible dextrin, galacto-oligosaccharide, xylo-oligosaccharide, arabino-oligosaccharide, arabinogalacto-oligosaccharide, gluco-oligosaccharide, glucomanno-oligosaccharide, galactomanno-oligosaccharide, mannan-oligosaccharide, chito-oligosaccharide, uronic acid oligosaccharide, sialyl-oligosaccharide and fuco-oligosaccharide.

4. The nutritional composition for use in the treatment of cow's milk protein allergy in cow's milk protein allergic infants according to claim 3, wherein the non-digestible oligosaccharide is a short-chain or long-chain fructo-oligosaccharide.

5. The nutritional composition for use in the treatment of cow's milk protein allergy in cow's milk protein allergic infants according to claim 1, comprising a lipid component and at least one digestible carbohydrate.

6. The nutritional composition for use in the treatment of cow's milk protein allergy in cow's milk protein allergic infants according to claim 1, wherein the composition comprises a total amount of protein of 5 to 25° A) based on dry weight of the composition.

7. The nutritional composition for use in the treatment of cow's milk protein allergy in cow's milk protein allergic infants according to claim 3, wherein the composition comprises 0.05 to 20 wt. % of the at least one non-digestible oligosaccharide based on dry weight of the composition.

8. The nutritional composition for use in the treatment of cow's milk protein allergy in cow's milk protein allergic infants according to claim 5, wherein the composition comprises 15 to 40% of the lipid component based on dry weight of the composition.

9. The nutritional composition for use in the treatment of cow's milk protein allergy in cow's milk protein allergic infants according to claim 1, which is an infant formula or a follow-on-formula.

10. The nutritional composition for use in the treatment of cow's milk protein allergy in cow's milk protein allergic infants according to claim 1, which is in the form of a dry powder or a ready to feed liquid.

11. A nutritional composition comprising at least one beta-lactoglobulin peptide comprising an amino acid sequence consisting of 18 to 30 amino acids and having an amino acid sequence selected from the group consisting of SEQ ID NO 1, SEQ ID NO 2, and SEQ ID NO 3, wherein the composition comprises 10 to 5000 µg of the at least one beta-lactoglobin peptide per g of total protein in the composition, and wherein the at least one beta-lactoglobulin peptide is for use in the treatment of cow's milk protein allergy in cow's milk protein allergic infants.

12. A nutritional composition comprising a protein component, a lipid component and digestible carbohydrates, wherein the protein component consists of i) the at least one beta-lactoglobulin peptide according to claim 1, and ii) at least one further protein component selected from the group consisting of extensively hydrolysed protein and free amino acids, wherein in sum of i) and ii) accounts for at least 95 wt. % of the protein component, and wherein the lipid component comprises at least 0.1 wt. % DHA based on total fatty acids.

13. The nutritional composition according to claim 12, comprising at least one non-digestible oligosaccharide, wherein the non-digestible oligosaccharide is a short-chain or long-chain fructo-oligosaccharide.

14. The nutritional composition according to claim 12, wherein the composition comprises a total amount of protein of 5 to 25° A) based on dry weight of the composition.

15. The nutritional composition according to claim 12, which is an infant formula or a follow-on-formula.

16. The nutritional composition according to claim 12, which is an infant formula or a follow-on-formula for use in feeding cow's milk protein allergic infants.

17. The nutritional composition for use in the treatment of cow's milk protein allergy in cow's milk protein allergic infants according to claim 1, wherein the at least one beta-lactoglobulin peptide is SEQ DI NO 3.

18. A nutritional composition comprising at least one beta-lactoglobulin peptide consisting of an amino acid sequence selected from the group consisting of SEQ ID NO 1, SEQ ID NO 2, and SEQ ID NO 3.

19. The nutritional composition according to claim 18, further comprising a protein component selected from the group consisting of hydrolysed whey protein, free amino acids, soy proteins, hydrolysed soy proteins, pea proteins, hydrolysed pea proteins, rice proteins, hydrolysed rice proteins, collagen, hydrolysed collagen, and mixtures thereof.

20. The nutritional composition according to claim 18, further comprising a lipid component and a carbohydrate component.

* * * * *